(12) United States Patent
Bush et al.

(10) Patent No.: US 6,363,288 B1
(45) Date of Patent: Mar. 26, 2002

(54) CS LEAD WITH SINGLE SITE SENSING AND DUAL SITE PACING

(75) Inventors: Mary Elizabeth Bush, Fremont, CA (US); Mae-Mae Shieh, Fontainebleau (FR)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/379,136

(22) Filed: Aug. 20, 1999

(51) Int. Cl.[7] .................................................. A61N 1/05
(52) U.S. Cl. ........................ 607/122; 607/123; 607/126; 600/381
(58) Field of Search ................................ 607/119, 121, 607/127, 123, 125; 600/374, 381

(56) References Cited

U.S. PATENT DOCUMENTS

| | | | |
|---|---|---|---|
| 3,937,226 A | 2/1976 | Funke | 128/419 D |
| 4,549,548 A | 10/1985 | Wittkampf et al. | 128/419 PG |
| 4,741,342 A | 5/1988 | Stotts | 128/419 P |
| 5,403,356 A | 4/1995 | Hill et al. | 607/14 |
| 5,405,375 A | 4/1995 | Ayers et al. | 607/122 |
| 5,466,254 A | 11/1995 | Helland | 607/123 |
| 5,514,161 A | 5/1996 | Limousin | 607/9 |
| 5,683,445 A | 11/1997 | Swoyer | 607/125 |
| 5,720,768 A | 2/1998 | Verboven-Nelissen | 607/9 |
| 5,755,761 A | * 5/1998 | Obino | 607/122 |
| 5,797,967 A | 8/1998 | KenKnight | 607/4 |
| 5,797,970 A | 8/1998 | Pouvreau | 607/9 |
| 5,978,704 A | * 11/1999 | Ideker et al. | 607/5 |
| 6,070,104 A | * 5/2000 | Hine et al. | 607/123 |
| 6,185,459 B1 | * 2/2001 | Mehra et al. | 607/14 |
| 6,201,994 B1 | * 3/2001 | Warman et al. | 607/123 |

OTHER PUBLICATIONS

J. Claude Daubert, et al.; "Biatrial Synchronous Pacing: A New Approach to Prevent Arrhythmias in Patients with Atrial Conduction Block"; Prevention of Tachyarrhythmias with Cardiac Pacing, Chapter 8; pp. 99–119.

S. Cazeau, et al.; "Four Chamber Pacing in Dilated Cardiomyopathy"; Pace, vol. 17, Nov. 1994, Part II; pp. 1974–1979.

Robert R. Brownlee, et al.; "Toward Optimizing a Preshaped Catheter and System Parameters to Achieve Single Lead DDD Pacing"; Pace, vol. 20, May 1997, Part I; pp. 1354–1358.

* cited by examiner

Primary Examiner—Jeffrey R. Jastrzab
(74) Attorney, Agent, or Firm—Steven M. Mitchell

(57) ABSTRACT

A system for providing medical electrical stimulation includes a pulse generator coupled to a lead having two electrodes for placement in the right atrium or for placement of one in the right atrium and one in the coronary sinus or coronary vein. In the preferred embodiment the surface area of the first electrode is smaller than that of the second electrode so that the sensed signal from the first electrode is less than that from the second. The system provides dual site pacing with essentially single site sensing without the use of extra switches, connectors, or adaptors.

20 Claims, 5 Drawing Sheets

CS LEAD WITH SINGLE SITE SENSING AND DUAL SITE PACING

FIELD OF THE INVENTION

The present invention generally relates to medical electrical stimulation, and more particularly, to a lead system for providing medical electrical stimulation to either two locations in a single atrium or to a site in each of the two atria of a patient's heart.

BACKGROUND OF THE INVENTION

Electrical stimulation of body tissues and organs is often used as a method of treating various pathological conditions. Such stimulation generally entails making electrical contact between body tissue and an electrical pulse generator through one or more stimulation leads. Various lead structures and various techniques for implanting these lead structures into body tissue and particularly the heart have been developed. For example, a transvenous endocardial lead is passed through a vein, with the assistance of a fluoroscope, into the heart where it may be held in electrical contact with the endocardium of the right atrium or ventricle.

The left chambers of the heart are presently not available for the implantation of long term transvenous leads due to risk of thrombus or clot formation. In particular, blood flows through the right side of the heart, through the lungs, through the left side of the heart and then through the rest of the body, including the brain, before returning again to the right side of the heart. Implanted objects often cause minor blood clots and thrombus to form in the blood. These may, on occasion, dislodge and be released into the bloodstream. Because the blood circulates directly from the left atrium and ventricle to the brain, any clots could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate the left side of the heart. As a result, transvenous lead placement into the coronary sinus (CS) or deeper into the great cardiac vein (GCV) or other coronary vein has recently become an important technique for cardiac pacing and defibrillation electrode implantation to gain electrical access to the left side of the heart. U.S. Pat. No. 4,932,407 to Williams; U.S. Pat. No. 5,099,838 to Bardy; and U.S. Pat. Nos. 5,348,021; 5,433,729; and 5,350,404 to Adams et al., incorporated herein by reference, describe inserting a lead through the right atrium and CS into one of the coronary veins. To implant a lead made in conformance with the present invention, the implanter passes the lead through a guide catheter, or introducer, until it is in or near the CS. This is done using a standard technique of stiffening the lead with a stylet, guiding the stiffened lead by hand through the right atrium (RA) and into or near the CS, aided by fluoroscopy. Following proper placement, any stiffening stylets or guide catheters are retracted.

As an example of placing leads into the CS, dual site right atrial pacing and biatrial pacing with the left atrium paced from the CS are being studied to reduce the incidence of paroxysms of atrial fibrillation. In a recent publication (Daubert et al., "Biatrial Synchronous Pacing: A New Approach to Prevent Arrhythmias in Patients with Atrial Conduction Block," from *Prevention of Tachyarrhythmias with Cardiac Pacing*, Futura Publishing Company, Inc., Armonk, N.Y., 1997, p. 111), dual site pacing has been done by pacing the RA cathodically and the LA anodically, using a Y adaptor. This composite dual atrial lead configuration detects three successive intracardiac signals: the RA electrogram, the LA electrogram, and a far field R wave sensed in the CS and corresponding to LV depolarization. If the pacemaker misinterprets these LV signals as originating in the atria, inappropriate inhibition or inappropriate triggering may occur, possibly creating a pacemaker-mediated tachycardia (PMT). In U.S. Pat. No. 5,514,161 to Limousin, a Y adaptor is used as described above, and software is used to deal with the ventricular signals in order to avoid such a PMT. It would be desirable to provide dual site pacing without requiring a Y adaptor or added connectors, and sensing only one atrial bipolar signal while rejecting ventricular signals.

As another example of placing leads into the CS or deeper, defibrillation electrodes within the CS have been shown to reduce atrial and ventricular defibrillation thresholds. U.S. Pat. No. 5,476,498 to Ayers shows an example of a lead having an atrial defibrillation electrode for implantation within the CS.

As yet another example of placing leads through the CS and deeper into a coronary vein, pacing the left ventricle (LO from within a coronary vein appears to improve hemodynamics in certain disease states such as heart failure. For example, in patients with dilated cardiomyopathy, electrical stimulation of both the right side and the left side of the heart has been shown to be of major importance to improve the patient's well-being and manage heart failure. See, for example, Cazeau et al., "Tour Chamber Pacing in Dilated Cardiomyopathy." PACE, November 1994, pp. 1974–79.

The functions desired of pacemakers and pacemaker/defibrillators currently require a large number of electrodes, a large number of lead connectors, and a large header with a large number of connector cavities. A solution is needed to provide needed features while not increasing device size and hardware to a clinically unacceptable level, and while still using standard (IS-1 and DF-1) connectors.

SUMMARY OF THE INVENTION

It is therefore an object of this invention to provide a lead or lead system that paces two sites simultaneously while sensing from essentially only one.

It is a further object of this invention to provide a lead or lead system that uses standard connectors.

It is a further object of this invention to reduce the hardware required without a reduction in desired features.

It is a further object of this invention to provide a lead system that does not require any adaptors.

It is a further object of this invention to provide a lead system for which no extra switches are required for switching between electrodes for pacing and sensing.

Briefly, the above and further objects and features of the present invention are realized by providing a system that uses one connector for both dual site pacing and single site sensing. In a first embodiment of the invention, the first pacing site is an RA location, and the second site is a second RA site near the CS os. In an alternative embodiment, the second site is an LA site through the CS. In one embodiment, a CS (LA) pacing electrode at the second site is electrically coupled to an RA electrode at the first site, with each acting as the cathode in its respective chamber. The anode for both is a second RA electrode, which may be either a dedicated ring electrode or a defibrillation electrode.

The present invention may include a CS defibrillation electrode, and the second site pacing electrode may be located either proximal or distal of the CS defibrillation electrode. If located distal of the CS defibrillation electrode, the electrode paces the LA; if proximal, the electrode may be positioned to pace the LA or a second site in the RA.

In the preferred embodiment, the lead is preshaped to encourage contact of the electrodes with the endocardium. For example, a curve in the portion of the lead to be positioned in the RA may be used to force the RA electrodes in contact with the RA endocardium. Likewise, one or more angles on the distal end of the CS lead may be used to force the LA electrode in contact with the CS oriented toward the LA. See for example U.S. Pat. No. 5,683,445 to Swoyer, which is incorporated herein by reference.

By keeping the LA (CS) pacing electrode very small, its current density can be kept high for pacing, while getting very little sensed signal from it (compared with the RA electrode). Increasing the impedance of the LA electrode as compared with the RA electrodes will accomplish this. Besides keeping the macroscopic surface area small, the microscopic surface area should also be kept small. In one embodiment of the invention, a smooth platinum or platinum iridium alloy tip is used to accomplish this in a lead that is stable within the CS in which sensing is not desirable. The RA electrodes are preferably porous to optimize sensing. In an alternative embodiment, one of the RA electrodes is replaced by an RA/SVC defibrillation electrode.

DETAILED DESCRIPTION OF THE INVENTION

Figure 1:
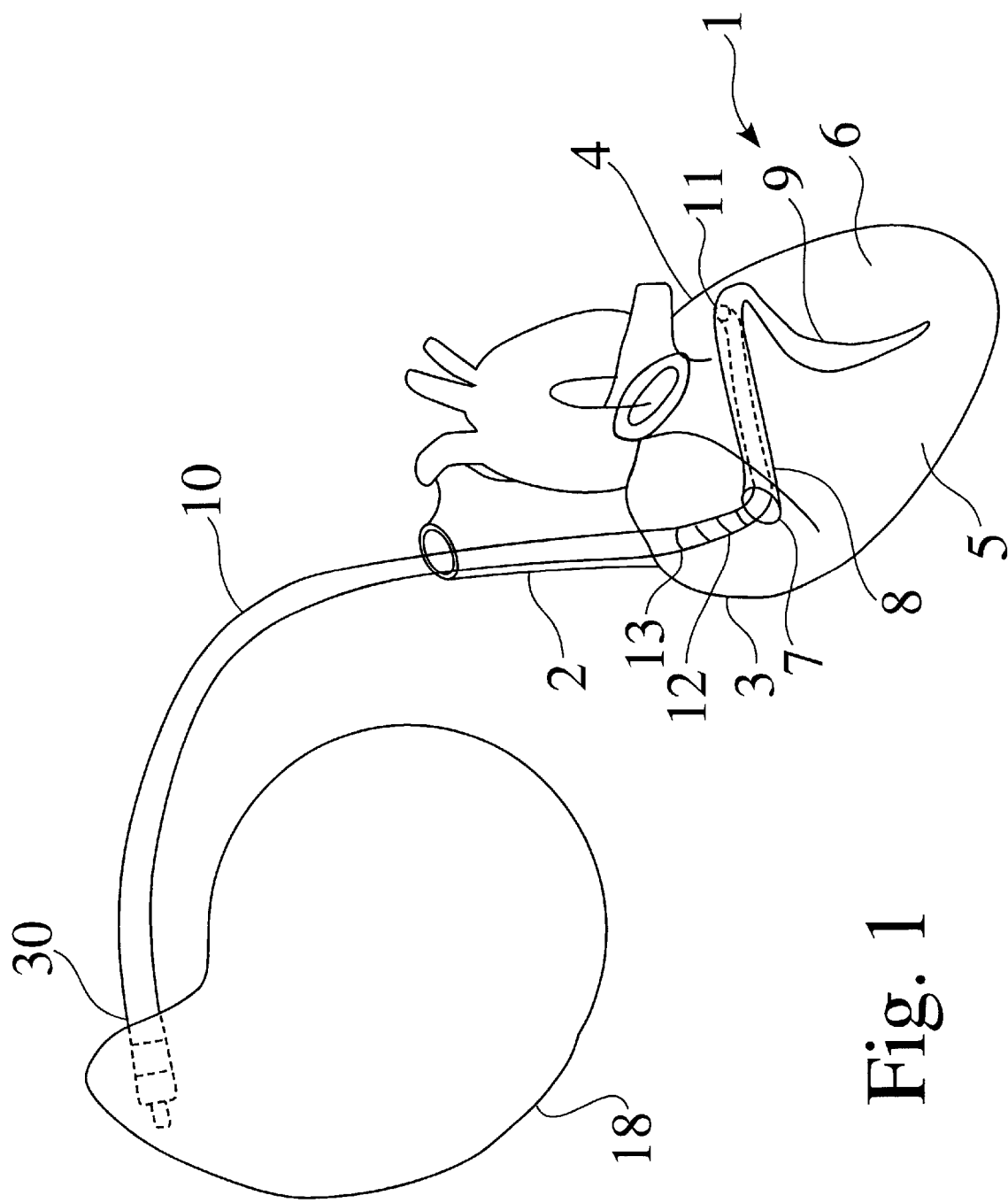
FIG. 1 is a plan view of a first embodiment of the cardiac lead of the present invention as implanted within the heart and with an electrode in the coronary sinus.

FIG. 1 shows a human heart 1 with the cardiac lead 10 of the present invention passing through the superior vena cava (SVC) 2, the right atrium (RA) 3, the coronary sinus os (CS os) 7 and into the coronary sinus (CS) 8 so that a first electrode 11 on lead 10 is implanted within the CS 8 and so that a second electrode 12 and a third electrode 13 are implanted within RA 3. Lead 10 is connected to pulse generator 18 using a coaxial bipolar connector 30. When positioned as shown, electrode 11 can be used to apply a stimulating pulse to the LA without the need of being in the left atrial chamber. Electrode 12 can be used to apply a stimulating pulse to the RA and electrodes 12 and 13 can be used to sense the electrical activity of the RA 3.

Figure 2:
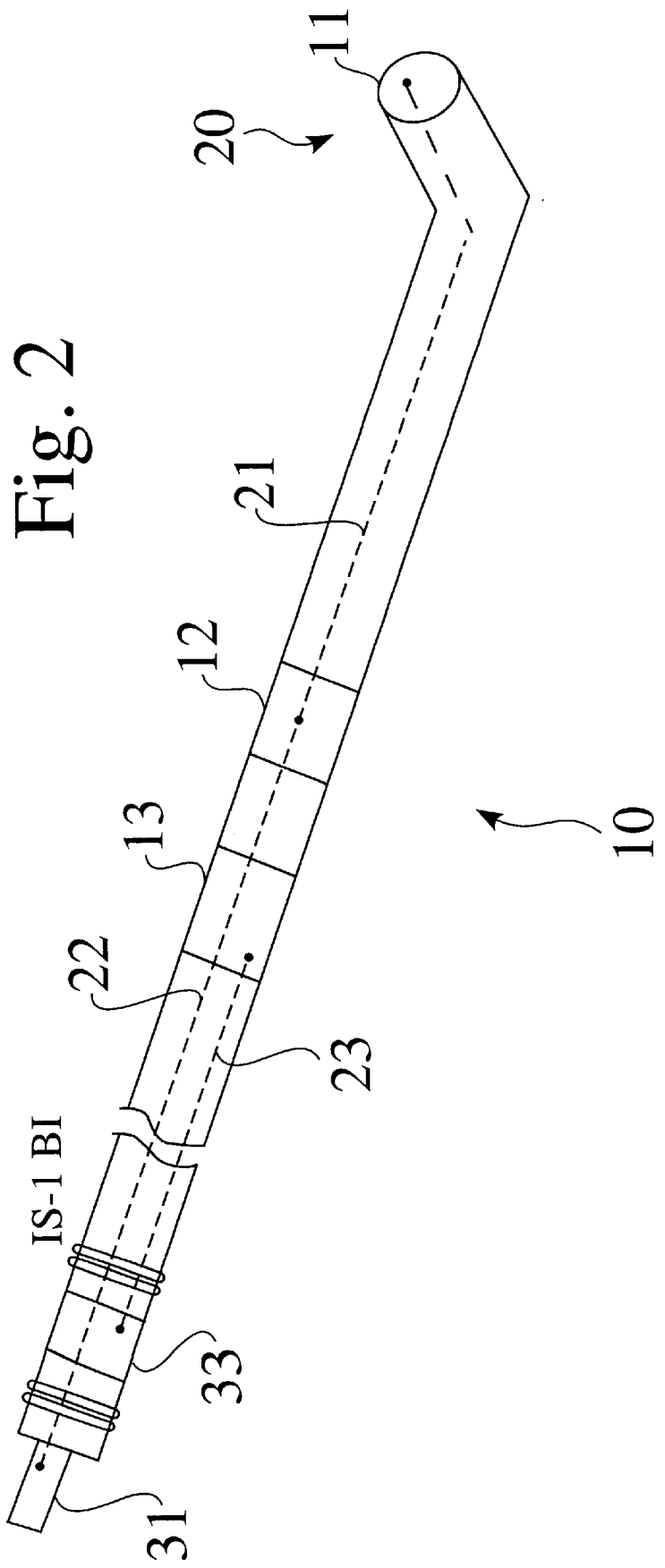
FIG. 2 is a schematic illustration of the cardiac lead shown in FIG. 1.

FIG. 2 shows in greater detail the structure of cardiac lead 10 shown in FIG. 1. As shown in FIG. 2, lead 10 includes an elongated body having a proximal end 19 and a distal end 20. Electrode 11 is shown as a tip electrode positioned at distal end 20 and is electrically coupled to a first conductor 21. Conductor 21 is, in turn, electrically coupled to a first contact 31 of coaxial bipolar connector 30. Electrode 11 may, alternatively be a ring electrode. Second electrode 12 is shown as a ring electrode and is electrically coupled to a second conductor 22, which is in turn electrically coupled to first contact 31. As shown, conductor 21 is coupled to first contact 31 via conductor 22, thereby saving space by not running parallel conductors. Alternatively, conductor 21 could extend all the way from first electrode 11 to first contact 31 without directly attaching to second electrode 12, and second conductor 22 could be completely separate from first conductor 21. This would, however, require more space. Electrode 12 preferably is spaced from electrode 11 along lead 10 by at least 20 mm so that pacing pulses will stimulate tissue in the vicinity of each electrode separately. Electrode 13 is shown as a ring electrode and is electrically coupled to a third conductor 23, which, in turn, is electrically coupled to a second contact 33 of coaxial bipolar connector 30. Electrode 13 may alternatively be a very large surface area electrode suitable for atrial and/or ventricular defibrillation as will be described in connection with FIG. 5 below. Electrode 13 preferably is spaced from electrode 12 by 2 mm to 15 mm such that bipolar signals obtained between electrodes 12 and 13 are optimum for sensing. As shown, connector 30 is a standard connector type, IS-1 BI, wherein first contact 31 is a pin that is typically used to couple to a pacemaker cathode, and second contact 33 is a ring that is typically used to couple to a pacemaker anode.

It is desirable to make the profile of the distal end of a lead implanted in a coronary vein as small as possible to limit occlusion of flow through the blood vessel when the lead is in place and to limit damage to the vessels. As shown in FIG. 2, lead 10 may be angled at distal end 20 to stabilize the lead within the CS and to bring electrode 11 in close contact with the tissue.

Figure 3:
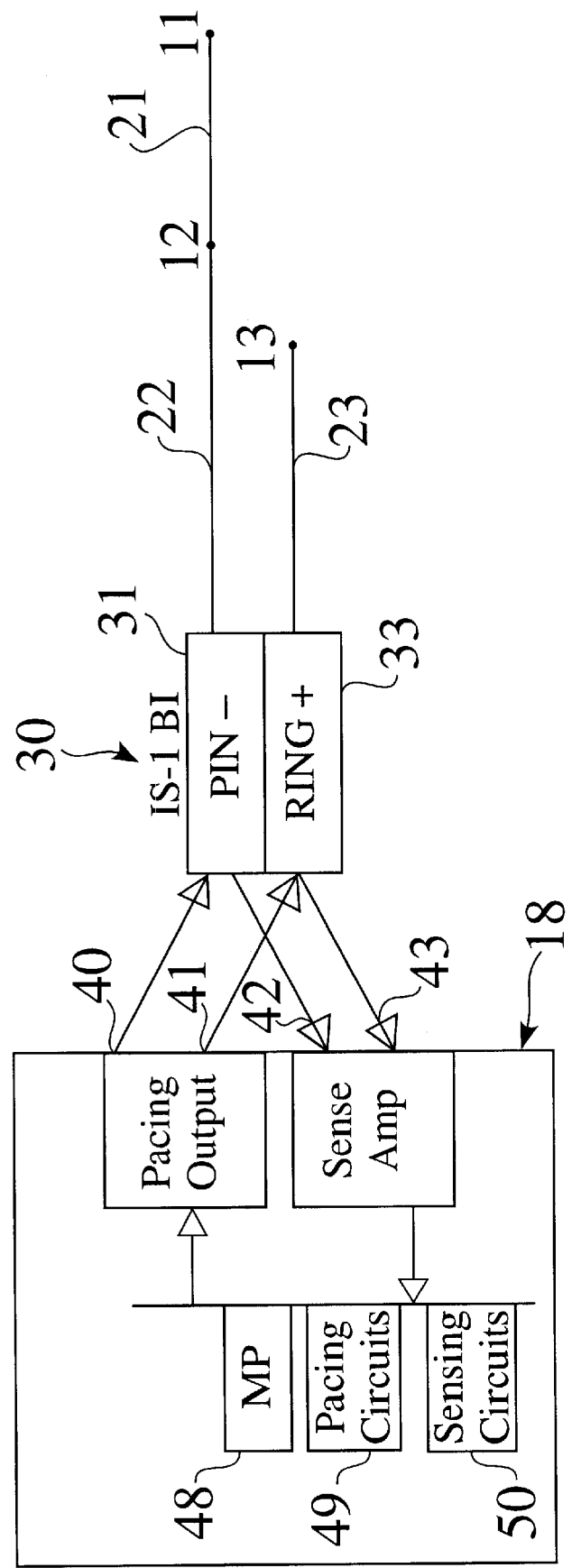
FIG. 3 is a block diagram of the electrical connections cardiac lead and pulse generator shown in FIG. 1.

FIG. 3 is a block diagram showing lead 10 connected to pulse generator 18. Pulse generator 18 includes a microprocessor 48, pacing circuits 49, and sensing circuits 50 as are well known in the art. Pulse generator 18 also includes first pacing output 40, second pacing output 41, first sense amplifier input 42, and second sense amplifier input 43. When connector 30 is inserted into the connector port (not shown) of pulse generator 18, first contact 31 is electrically coupled to first pacing output 40 and to first sense amplifier 42, and second contact 33 is electrically coupled to second pacing output 41 and to second sense amplifier 43. In this way, electrodes 11 and 12 become coupled to first pacing output 40 and to first sense amplifier 42, and electrode 13 becomes coupled to second pacing output 41 and to second sense amplifier 43. In the embodiment shown in FIG. 3, first contact 31 is a pin coupled to the pacing output cathode, and second contact 33 is a ring coupled to the pacing output anode.

It is advantageous to pace from both electrode 11 and electrode 12. However, the pacing threshold is generally higher when pacing the LA through the CS as compared with pacing the RA. Therefore, it is desirable to keep the current density higher at electrode 11 than at electrode 12 to even out the pacing thresholds. Furthermore, no stimulation is desired at electrode 13. Still further, in order to avoid sensing ventricular signals, it is desirable to have all sensed signal come from electrodes 12 and 13, with as little as possible from electrode 11. By keeping the LA (CS) pacing electrode very small, its current density can be kept high for pacing, while getting very little sensed signal from it (compared with the RA electrodes). This can be done by increasing the impedance of the LA electrode as compared with the RA electrodes. One effective method for doing this is to make both the macroscopic surface area and the microscopic surface area smaller than that of electrodes 12 and 13. A smooth platinum tip is preferred for this application if the lead is already stable within the CS and sensing is not desirable. It will also be easier to remove than a porous tip, should the need arise. The RA electrodes 12 and 13 are preferably porous to optimize sensing.

Figure 4:
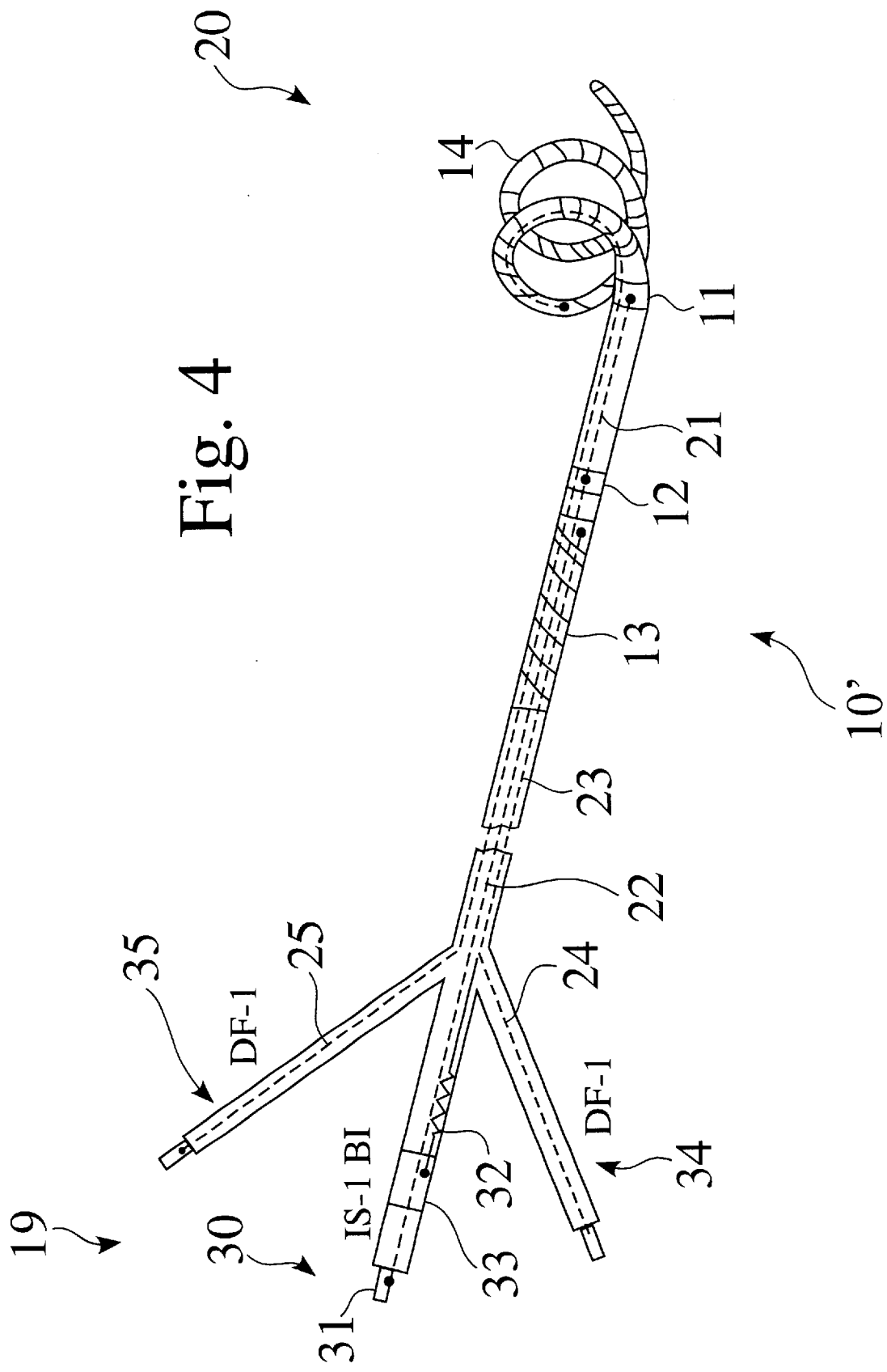
FIG. 4 is a schematic illustration of an alternative embodiment of the cardiac lead of the present invention.

FIG. 4 shows an alternative embodiment of lead 10' that provides additional functions as compared to the embodiment of FIGS. 1–3. As in the previously described embodiment, electrodes 11 and 12 are coupled to first contact 31 of connector 30 via conductors 21 and 22. Electrode 12 preferably is spaced from electrode 11 along lead 10' by at least 20 mm so that pacing pulses will stimulate tissue in the vicinity of electrode 11 and electrode 12 separately. Electrode 11 is positioned on lead 10' to pace the LA from within the CS. Electrode 12 is positioned on lead 10' to pace the RA. Alternatively, electrodes 11 and 12 may be positioned to pace different parts of the RA.

Electrode 13 is shown as a large surface area electrode for placement within the RA and/or SVC and suitable for atrial and/or ventricular defibrillation as well as for a "reference electrode" for pacing and sensing. Electrode 13 is electrically coupled a first high voltage connector 34 via low resistance conductors 23 and 24. In this case connector 34 is shown as a standard DF-1 connector. Low resistance conductor 24 is an extension of low resistance conductor 23; alternatively, low resistance conductor 24 may be a separate conductor coupled to low resistance conductor 23. Low resistance conductor 23 is coupled also to second contact 33 of connector 30 via a high resistance conductor 32 (shown schematically as a resistor).

Even more electrodes and conductors can be added for sensing, pacing or defibrillating as desired. For example, a large surface area defibrillation electrode 14 for implantation within the CS or great cardiac vein is shown on the distal portion of lead 10'. Preferably, defibrillation electrode 14 has a shape that stabilizes lead 10' within the CS. The distal portion 20 of lead 10' that is intended for placement through the CS os preferably has a smaller diameter than the proximal portion 19. Defibrillation electrode 14 is coupled to a second high voltage connector 35 via a low resistance conductor 25. Alternatively or additionally, lead 10' includes one or more pacing or sensing electrodes for implantation within the CS for pacing the LV.

Figure 5:
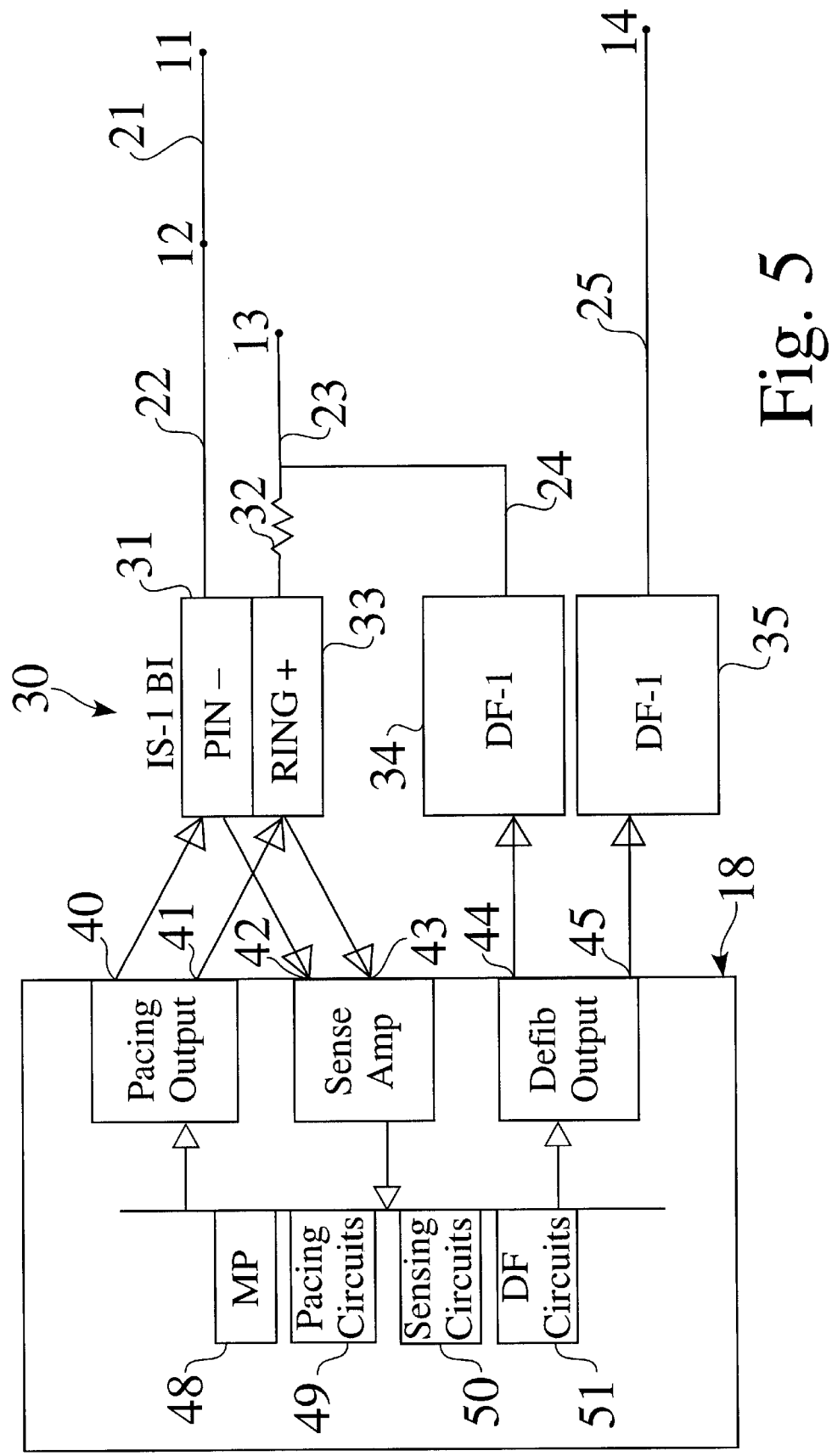
FIG. 5 is a block diagram of the cardiac lead shown in FIG. 4 as connected to a pulse generator.

FIG. 5 is a block diagram showing lead 10' of FIG. 4 connected to pulse generator 18'. Pulse generator 18' includes a microprocessor 48, pacing circuits 49, sensing circuits 50, and defibrillation circuits 51 as are well known in the art. Pulse generator 18' also includes first pacing output 40, a second pacing output 41, a first sense amplifier input 42, a second sense amplifier input 43, a first defibrillation output 44, and a second defibrillation output 45. When connector 30 is inserted into the connector port (not shown) of pulse generator 18', first contact 31 is electrically coupled to first pacing output 40 and to first sense amplifier 42, and second contact 33 is electrically coupled to second pacing output 41 and to second sensing input 43. Furthermore, when first high voltage connector 34 is inserted into the first high voltage connector port (not shown) of pulse generator 18', third electrode 13 is electrically coupled to first defibrillation output 44. When second high voltage connector 35 is inserted into the second high voltage connector port (not shown) of pulse generator 18', fourth electrode 14 is electrically coupled to second defibrillation output 45. Defibrillation outputs 44 and 45 may be of opposite polarity, or may be of the same polarity to be used in conjunction with other defibrillation electrodes.

Electrode 13 is electrically coupled to a first high voltage connector 34 via low resistance conductors 23 and 24. Low resistance conductor 23 is coupled also to second contact 33 of connector 30 via a high resistance conductor 32. The resistance that is added in the pacing/sensing leg by high resistance conductor 32 protects the pacing and sensing circuits during defibrillation.

The foregoing discussion is intended to illustrate various preferred arrangements for meeting the objectives of the present invention. For example, more than two sites may be paced simultaneously. Those skilled in the art can make modifications and variations without departing from the invention. Accordingly, the invention is limited only by the scope of the following claims.

What is claimed:

1. A medical lead comprising:
   (a) a coaxial connector having first and second electrical contacts;
   (b) a first electrode electrically coupled to said first electrical contact of said coaxial connector;
   (c) a second electrode electrically coupled to said first electrical contact of said connector; and
   (d) a third electrode electrically coupled to said second electrical contact of said connector;
   wherein each of said first, second, and third electrodes has a microscopic surface area and wherein said first electrode microscopic surface area is smaller than said second electrode microscopic surface area.

2. The medical lead of claim 1 wherein said connector is a coaxial bipolar connector.

3. The medical lead of claim 1 wherein said second electrode is spaced between 2 mm and 15 mm from said third electrode.

4. The medical lead of claim 1 wherein said first electrode is spaced at least 20 mm from said second electrode.

5. The medical lead of claim 1 wherein each of said first, second, and third electrode has an impedance and wherein said first electrode is located distal of said second and third electrodes and wherein said first electrode impedance is higher than said second electrode impedance.

6. The medical lead of claim 1 wherein said first electrode is made of smooth, polished material chosen from the group consisting essentially of platinum and platinum iridium alloy.

7. The medical device of claim 1 where in said second electrode has a porous surface.

8. The medical lead of claim 1 wherein each of said first, second, and third electrodes has a macroscopic surface area and wherein said third electrode macroscopic surface area is greater than said first electrode macroscopic surface area and greater than said second electrode macroscopic surface area.

9. The medical lead of claim 8 wherein said first electrode macroscopic surface area is less than said second electrode macroscopic surface area.

10. The medical lead of claim 1 and further including a fourth electrode coupled to a high voltage connector and located distal of said second and third electrodes.

11. The medical lead of claim 10 wherein said fourth electrode is positioned on said lead between said first electrode and said second electrode.

12. The medical lead of claim 10 wherein said fourth electrode is positioned on said lead distal of said first and second electrodes.

13. The medical lead of claim 10 and further including a fifth electrode positioned on said lead distal of said fourth electrode and adapted to pace the patient's left ventricle.

14. The medical lead of claim 1 wherein said lead is curved to encourage contact of said second electrode with patient's right atrium.

15. The medical lead of claim 1 wherein said connector is a standard IS-1 bipolar connector and wherein said first contact comprises a pin and wherein said second contact comprises a ring.

16. A medical device system comprising:
   (a) a pulse generator having a connector port, said connector port having a cathode contact and an anode contact, wherein said pulse generator applies pacing pulse voltages across said cathode contact and said anode contact, and wherein said pulse generator senses incoming signals across said cathode contact and said anode contact; and
   (b) a lead having a lead connector, said lead connector having a lead connector cathode contact for contacting said connector port cathode contact and a lead connector anode contact for contacting said connector port anode contact, said lead further comprising
      (i) a first electrode electrically coupled to said lead connector cathode contact;
      (ii) a second electrode electrically coupled to said lead connector cathode contact; and
      (iii) a third electrode electrically coupled to said lead connector anode contact;
   wherein each of said first, second, and third electrodes has a microscopic surface area and wherein said first electrode microscopic surface area is smaller than said second electrode microscopic surface area.

17. The medical device system of claim 16 wherein said connector port anode contact comprises a ring contact, and wherein said connector port cathode contact comprises a pin contact, and wherein said lead connector comprises a coaxial bipolar connector, and wherein said lead connector cathode contact comprises a lead connector pin, and wherein said lead connector anode contact comprises a lead connector ring.

18. A medical lead comprising:
   (a) a connector having first and second electrical contacts;
   (b) a first electrode electrically coupled to said first electrical contact of said connector;
   (c) a second electrode electrically coupled to said first electrical contact of said connector; and
   (d) a third electrode electrically coupled to said second electrical contact of said connector, wherein each of said first, second, and third electrode has an impedance and wherein said first electrode is located distal of said second and third electrodes and wherein said first electrode impedance is higher than said second electrode impedance;
   wherein each of said first, second, and third electrodes has a microscopic surface area and wherein said first electrode microscopic surface area is smaller than said second electrode microscopic surface area.

19. A medical lead comprising:
   (e) a connector having first and second electrical contacts;
   (f) a first electrode electrically coupled to said first electrical contact of said connector;
   (g) a second electrode electrically coupled to said first electrical contact of said connector; and
   (h) a third electrode electrically coupled to said second electrical contact of said connector, wherein each of said first, second, and third electrode has a microscopic surface area and wherein said first electrode microscopic surface area is smaller than said second electrode microscopic surface area.

20. A medical lead comprising:
   (a) a coaxial connector having first and second electrical contacts;
   (b) a first electrode electrically coupled to said first electrical contact of said coaxial connector;
   (c) a second electrode electrically coupled to said first electrical contact of said connector;
   (d) a third electrode adapted to deliver defibrillation energy and electrically coupled to said second electrical contact of said connector;
   (e) a high voltage connector electrically coupled to said third electrode; and
   (f) a resistor connected in series between said third electrode and said second contact of said connector.

* * * * *